United States Patent [19]
Cooper et al.

[11] Patent Number: 5,236,900
[45] Date of Patent: Aug. 17, 1993

[54] ANTI-FUNGAL AGENTS

[75] Inventors: Alan B. Cooper, West Caldwell; Anil K. Saksena, Upper Montclair; Raymond Lovey, West Caldwell; Viyyoor Girijavallabhan, Parsippany; Ashit Ganguly, Upper Montclair, all of N.J.

[73] Assignee: Schering Corporation, Kenilworth, N.J.

[21] Appl. No.: 747,588

[22] Filed: Aug. 20, 1991

[51] Int. Cl.$^5$ .............. A61K 31/70; A61K 37/02; C07H 19/06
[52] U.S. Cl. ........................ 514/19; 514/50; 514/252; 514/43; 536/28.7; 536/28.8; 544/311; 544/312
[58] Field of Search ............ 548/262.2, 318, 336, 548/266.4; 544/311, 312, 374, 408, 359, 372, 373, 310, 405; 514/210, 252, 274, 383, 392, 397, 43, 50, 19; 536/23, 24, 28.7, 28.8

[56] References Cited

U.S. PATENT DOCUMENTS

| | | | |
|---|---|---|---|
| 4,158,608 | 6/1979 | Sähn et al. | 536/24 |
| 4,315,922 | 2/1982 | Hagenmaier et al. | 536/24 |
| 4,552,954 | 11/1985 | Moerchler et al. | 536/23 |
| 4,585,761 | 4/1986 | Zahner et al. | 536/24 |
| 4,914,087 | 4/1990 | Hector et al. | 536/24 |

FOREIGN PATENT DOCUMENTS 330923 9/1989 European Pat. Off.
1492111 5/1969 Fed. Rep. of Germany.

OTHER PUBLICATIONS

*Antimicrobial Agents and Chemotherapy*, Apr., 1990, pp. 587–593.
*J. Org. Chem.*, 1986, 51, pp. 2307–2314, Boehm et al.
*Antimicrobial Agents and Chemotherapy*, Nov. 1983, pp. 787–796.
Shenbagamurthi *J. Med Chem*, 1986, 29, pp. 802–809.
J. Med Chem, 1988, 31, pp. 650–656, Khare et al.
*J. Org. Chem.*, 1990, 55, pp. 3372–3787, Garner et al.
Tetrahedron Letters, vol. 30, 38, pp. 5065–5068 (1984) Garner et al; JACS, Jul. 28, 1971, pp. 3812–3813.
New Synthetic Polyoxin Analogs for Chitin Synthesis Inhibition, Smith et al., Chitin Nat. Technol. 3rd, (1985) pp. 197–202.
J. Med. Chem. (1986), 29, 802–809.
J. Org. Chem. (1986), 51, 2307–2314.
CA 106: 192579x (1987).
Advanced Organic Chemistry Third Edition pp. 473–474 Carey et al. Plenum Press (1986).
An Introduction to Organic Chemistry pp. 454–455 Holden-Day, Inc. Reusch (1986).

*Primary Examiner*—Robert W. Ramsuer
*Attorney, Agent, or Firm*—James R. Nelson; Eric S. Dicker; Matthew Boxer

[57] ABSTRACT

Compounds of the formula

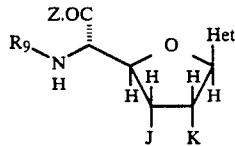

I wherein $R_9$, J, K, Z and Het are as set forth herein as described.

The compounds of formula I are useful as agents in the treatment of fungal infections.

9 Claims, No Drawings

ANTI-FUNGAL AGENTS

SUMMARY OF THE INVENTION

The invention relates to compounds of the formula:

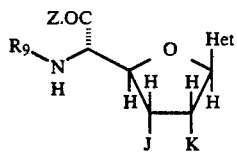   I or pharmaceutically acceptable salts thereof wherein:
Het is

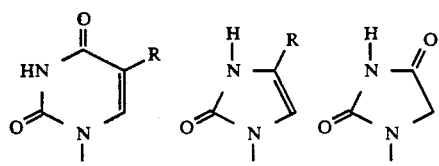

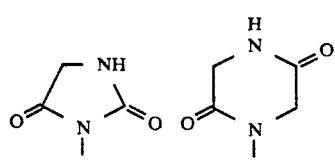

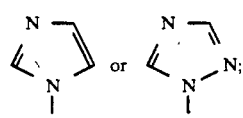

R is H, COOH; $C_1$-$C_{12}$ alkyl; CHO; CN; $CH_2OH$; or $CONH_2$;

$R_9$ is a natural amino acid substituted at the 2-amino position by H, a natural amino acid, or a metabolizable group;

J and K are the same or different and are independently selected from the group consisting of OH, H, Br, Cl and F;

Z is $R_5NR_6$,

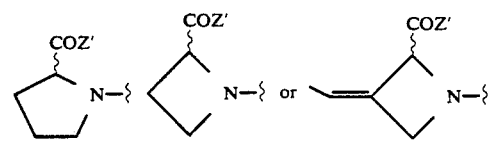

wherein Z' is $R_5NR_6$, $R_5$ is H, or a saturated or unsaturated $C_6$-$C_{18}$ aliphatic side chain or a hydroxylated $C_6$-$C_{18}$ aliphatic side chain, $R_6$ is H, OH, O-benzyl, O-aryl, $OC_4$-$C_{14}$ alkyl, $C_1$-$C_{12}$ alkyl, phenyl or substituted phenyl or CO—$R_7$; and $R_7$ is $C_1$-$C_{16}$ alkyl, aryl or alkylaryl.

Preferred are compounds of formula I wherein J and K are both OH.

Especially preferred are compounds of formula I wherein Het is uracil.

Preferred are compounds of formula I wherein $R_9$ is a natural amino acid with the L-configuration.

Preferred are compounds of formula I wherein Het is uracil.

As used herein, UR denotes uracil. Uracil has the structure:

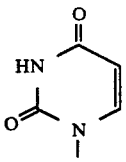

The term UPOC denotes uracil polyoxin C. The structural formula for UPOC is

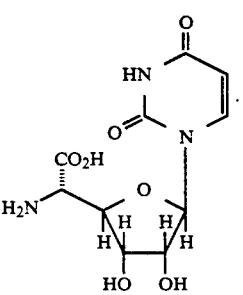

Alkyl denotes straight or branched hydrocarbon chains, which contain from 1 to 20 carbon atoms. Representative examples include methyl, ethyl, propyl, decyl, dodecyl and the like. Alternatively, the number of carbon atoms in a particular alkyl may be specified. For example, $C_1$-$C_6$ alkyl refers to an alkyl which may have one to six carbon atoms.

Alkoxy denotes —O-alkyl wherein alkyl is as described above.

The term natural amino acid denotes the following amino acids, glycine and the following acids which have an L-configuration: valine, leucine, isoleucine, serine, aspartic acid, asparagine, glutamic acid, histidine, alanine, proline, phenylalanine, tryptophan, methionine, threonine, cysteine, tyrosine, glutamine, lysine and arginine which are also referred to respectively by the following abbreviations:

Gly, Val, Leu, Ile, Ser, Asp, Asn, Glu, His, Ala, Pro, Phe, Trp, Met, Thr, Cys, Tyr, Gln, Lys and Arg.

The term metabolizable group denotes any group which under metabolizable conditions (that is, when subjected to metabolic enzymes and the like) will be cleaved off. An example is

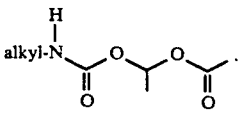

The term saturated aliphatic side chain denotes a saturated side chain containing only carbons and hydrogen. The saturated aliphatic side chain may contain up to 20 carbon atoms. Alternatively, the number of carbon atoms in an saturated aliphatic side chain may be specified. For example, a saturated $C_6$-$C_{18}$ aliphatic side chain denotes a saturated aliphatic side chain having from 6 to 18 carbon atoms. The saturated aliphatic side chain may contain within the chain up to three of any combination of the heteroatoms O, S, or N, with the proviso that such heteroatoms cannot be adjacent to each other in the chain.

The term unsaturated aliphatic side chain denotes an aliphatic side chain containing up to three double or triple bonds or any combination thereof. For example an unsaturated aliphatic side chain may contain three double bonds, two double bonds and one triple bond, one double bond and two triple bonds, or three triple bonds. The unsaturated aliphatic side chain may contain up to 20 carbon atoms. Alternatively, the number of carbon atoms in an unsaturated aliphatic side chain may be specified. For example, a unsaturated $C_6$-$C_{18}$ aliphatic side chain denotes an unsaturated aliphatic side chain having from 6 to 18 carbon atoms. The unsaturated aliphatic side chain may contain within the chain up to three of any combination of the heteroatoms O, S, or N, with the proviso that such heteroatoms cannot be adjacent to each other in the chain.

A hydroxylated aliphatic side chain denotes an aliphatic side chain as described above, wherein up to 3 hydrogens are replaced by OH. The hydroxylated aliphatic side chain may contain up to 20 carbon atoms. Alternatively, the number of carbon atoms in an hydroxylated aliphatic side chain may be specified. For example, a hydroxylated $C_6$-$C_{18}$ aliphatic side chain denotes an hydroxylated aliphatic side chain having from 6 to 18 carbon atoms. The hydroxylated aliphatic side chain may contain within the chain up to three of any combination of the heteroatoms O, S, or N, with the proviso that such heteroatoms cannot be adjacent to each other in the chain.

Aryl denotes a mono or bi-cyclic aromatic system. Examples of preferred aryl groups include those having from 6 to 14 carbon atoms. Representative examples include phenyl, 1-naphthyl, 2-naphthyl, and indanyl. The aryl group may contain additional substituents selected from the group consisting of: halogen atoms (e.g. Cl, Br, F and/or I), alkoxy, alkyl, and amino.

Alkylaryl denotes an aryl as described herein, wherein one of the hydrogens of the aryl is substituted by an alkyl as described herein.

A substituted phenyl refers to a phenyl bearing up to three substituents independently selected from the group consisting of —S-alkyl, —S—H, amino, $NO_2$, and O-alkyl; and up to five substituents independently selected from the group consisting of fluoro, alkyl, and OH.

As used herein, a boldfaced bond, ◂▬ denotes a bond which comes up out of the plane of the page. A dashed bond, ⁞⁞⁞⁞⁞ denotes a bond which comes down below of the plane of the page. A curved bond, ⌒⌒⌒ denotes a racemic mixture.

Exemplary compounds of the invention include:

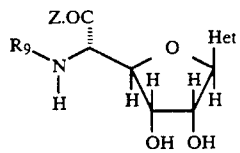

| No. | $R_9$ | Z.OC | Het |
|---|---|---|---|
| 1. | $CH_3$-$CH(CH_3)$-$CH_2$-$CH(NH_2)$-CO | $CONH(CH_2)_{11}CH_3$ | UR |
| 2. | $CH_3$-S-$CH_2$-$CH_2$-$CH(NH_2)$-CO | $CONH(CH_2)_{11}CH_3$ | UR |
| 3. | $(CH_3)_2CH$-$CH(NH_2)$-CO | $CONH(CH_2)_{11}CH_3$ | UR |
| 4. | $CH_3$-$CH(CH_3)$-$CH_2$-$CH(NH_2)$-CO | $CONH(CH_2)_{11}CH_3$ | UR |
| 5. | $CH_3$-$CH(CH_3)$-$CH_2$-$CH(NH_2)$-CO | $CONH(CH_2)_{13}CH_3$ | UR |
| 6. | $CH_3$-$CH(CH_3)$-$CH_2$-$CH(NH_2)$-CO | $CONH(CH_2)_9CH_3$ | UR |

-continued $$\text{R}_9\text{-NH-CH(Z.OC)-CH(H)-O-CH(Het)-CH(H)-CH(OH)-CH(OH)}$$ (ring structure with H, OH, OH, Het substituents)

| No. | R₉ | Z.OC | Het |
|---|---|---|---|
| 7. | CH₃-S-CH₂CH₂-CH(NH₂)-CO- | CH₃O₂C—(CH₂)₁₁—NHCO | UR |
| 8. | CH₃-S-CH₂CH₂-CH(NH₂)-CO- | CH₃(CH₂)₁₂NHCO | UR |
| 9. | CH₃-S-CH₂CH₂-CH(NH₂)-CO- | HO₂C—(CH₂)₁₁—NHCO | UR |
| 10. | CH₃-S-CH₂CH₂-CH(NH₂)-CO- | CH₃(CH₂)₉-CH(OH)-CH₂-NHCO | UR |
| 11. | Tryptophanyl (indole-CH₂-CH(NH₂)-CO-) | CONH(CH₂)₁₁CH₃ | UR |
| 12. | CH₃-S-CH₂CH₂-CH(NH—Leu)-CO- | CONH(CH₂)₁₁CH₃ | UR |
| 13. | Prolyl (pyrrolidine-2-CO-) | CONH(CH₂)₁₁CH₃ | UR |
| 14. | CH₃-S-CH₂CH₂-CH(NH₂)-CO- | CH₃CH₂—C≡C—(CH₂)₇—NHCO | UR |
| 15. | CH₃-S-CH₂CH₂-CH(NH₂)-CO- | C₆H₅—(CH₂)₃—O—(CH₂)₆—NCO | UR |
| 16. | CH₃-S-CH₂CH₂-CH(NH₂)-CO- | CH₃—C≡C—(CH₂)₉—NCO | UR |
| 17. | CH₃-S-CH₂CH₂-CH(NH₂)-CO- | CH₃CH₂CH₂—C≡C—(CH₂)₇—NCO | UR |
| 18. | CH₃-S-CH₂CH₂-CH(NH₂)-CO- | CH₃CH₂—CH=CH—(CH₂)₈—NHCO | UR |
| 19. | (CH₃)₂CH-CH(CH₃)-CH(NH₂)-CHO | CH₃(CH₂)₃—CH=CH—(CH₂)₆—NHCO | UR |

-continued

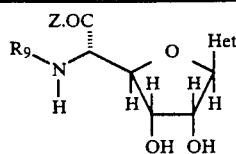

| No. | R9 | Z.OC | Het |
|---|---|---|---|
| 20. | (CH3)(CH3CH2)CH-CH(NH2)-CHO | CONH(CH2)10CH3 | UR |
| 21. | (CH3)(CH3CH2)CH-CH(NH2)-CHO | CH3CH2-CH=CH-(CH2)8-NCO | UR |
| 22. | (CH3)(CH3CH2)CH-CH(NH2)-CHO | CH3-CH=CH-(CH2)9-NCO | UR |
| 23. | (CH3)2CH-CH(NH2)-CHO | CONH(CH2)11CH3 | Me-UR |
| 24. | CH3S-(CH2)2-CH(NH2)-CHO | CH3S-(CH2)10-NHCO | UR |
| 25. | H2N-CO-(CH2)2-CH(NH2)-CO | CONH(CH2)11CH3 | UR |
| 26. | CH3-CH(NH2)-CO | CONH(CH2)11CH3 | UR |
| 27. | CH3S-(CH2)2-CH(NH2)-CO | NC-(CH2)10-NHCO | UR |
| 28. | CH3S-(CH2)2-CH(NH2)-CO | OHC-NH-(CH2)10-NHCO | UR |
| 29. | CH3S-(CH2)2-CH(NH2)-CO | (1,2,4-triazol-1-yl)-(CH2)10-NHCO | UR |
| 30. | (CH3)(CH3CH2)CH-CH(NH2)-CO | CH3CH2-CH=CH-(CH2)10-NHCO | UR |
| 31. | (CH3)(CH3CH2)CH-CH(NH2)-CO | CH3(CH2)11-CH(OH)-CH2-NHCO | UR |

-continued

| No. | $R_9$ | Z.OC | Het |
|---|---|---|---|
| 32. | (CH3)2CHCH(NH2)-CO- | $CH_3S(CH_2)_{10}NHCO$ | UR |
| 33. | (CH3)2CHCH(NH2)-CO- | $CH_3(CH_2)_4CH(NHCO-)(CH_2)_4CH_3$ | UR |

Preferred compounds of the invention are:

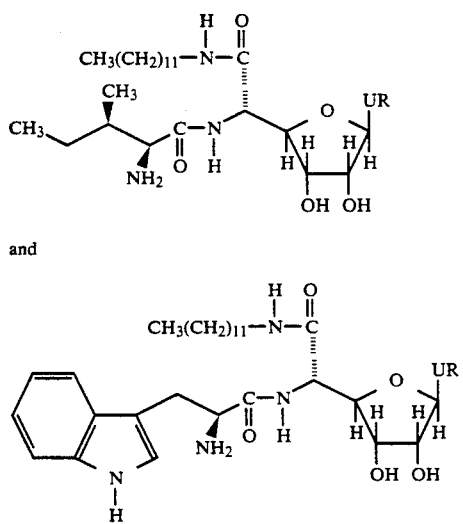

and or a pharmaceutically acceptable salt thereof.

The most preferred compound of the invention is

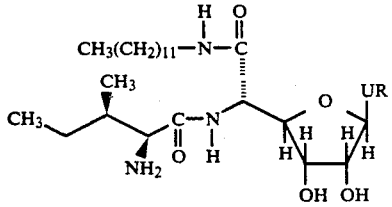

or a pharmaceutically acceptable salt thereof.

The invention also relates to a pharmaceutical composition which comprises a compound of formula I in combination with a pharmaceutically acceptable carrier material.

The invention also relates to a method for treating fungi which comprises administering to a mammal in need of such treatment an effective amount of a compound of formula I for such purpose.

DETAILED DESCRIPTION OF THE INVENTION

Asymmetric centers exist in compounds of formula I of the invention. Accordingly, compounds of formula I include stereoisomers.

All such isomeric forms and mixtures thereof are within the scope of the present invention. Unless otherwise indicated, the methods of preparation disclosed herein may result in product distributions which include all possible structural isomers, although it is understood that physiological response may vary according to stereochemical structure. The isomers may be separated by conventional means such as fractional crystallization or HPLC (high performance liquid chromatography).

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

The compounds of formula I form pharmaceutically acceptable salts. The preferred pharmaceutically acceptable salts are nontoxic acid addition salts formed by adding to a compound of the invention about a stoichiometric amount of a mineral acid, such as HCl, HBr, $H_2SO_4$ or $H_3PO_4$ or of an organic acid such as acetic, propionic, valeric, oleic, palmitic, stearic, lauric, benzoic, lactic, paratoluenesulfonic, methane sulfonic, citric, maleic, fumaric, succinic and the like, respectively.

The compounds of formula I above may be prepared by the methods described below with reference to Formula Schemes 1 and 2.

FORMULA SCHEME 1

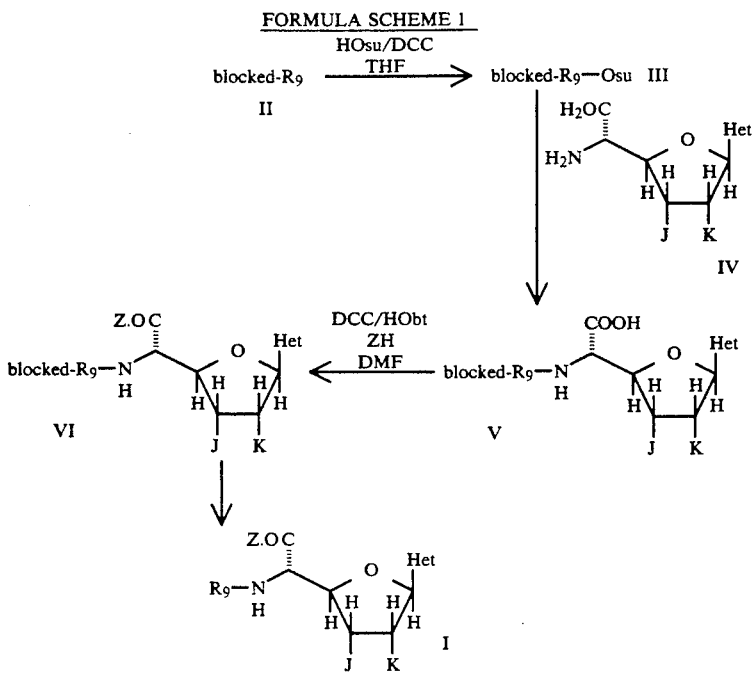

wherein $R_5$, $R_6$, $R_9$, J, K, Z, and Het are as described herein.

As used herein Osu denotes N-oxysuccinimide, HOsu denotes N-hydroxysuccinimide, DCC denotes 1,3-dicyclohexylcarbodiimide, HObt denotes N-hydroxybenztriazole, DMF denotes N,N-dimethylformamide, (BOC)$_2$O denotes di-tert.butyldicarbonate. Blocked-$R_9$ denotes a natural amino acid that has a blocking group such as tert-butoxycarbonyl (BOC) or benzyloxycarbonyl (CBZ) on the nitrogen atom. Compound denoted by Blocked-$R_9$ are known, can be prepared by known methods, or their preparation is described herein.

Examples of blocked $R^9$ include

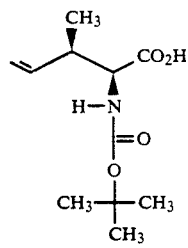

and

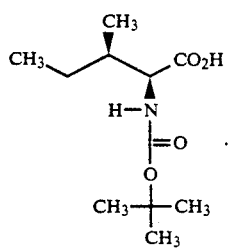

The compounds of formulas II and IV are known, can be prepared in accordance with known methods, or else their preparation is described herein.

A compound of formula II may converted to the corresponding N-oxysuccinimide ester of formula III thereof by reaction with N-hydroxysuccinimide in an aprotic, organic solvent such as N,N-dimethylformamide, acetonitrile, ethyl acetate, methylene chloride, or more preferably, tetrahydrofuran in the presence of a carbodiimide such as 1,3-dicyclocarbodiimide, and at a temperature in the range of about 0° to about 40° C. or more preferably 20° C. The resulting ester of formula III may be isolated by conventional means such as crystallization or chromatography, or it may be used directly in the next step of a synthesis of this invention.

Procedure A

A N-oxysuccinimide ester of formula III may be reacted with a uracil polyoxin C compound of formula IV

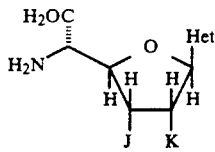

wherein J, K, and Het are as described above, to obtain a compound of formula V. The reaction is run in apolar, aprotic, organic solvent such as N,N-dimethylformamide, acetonitrile, tetrahydrofuran, or more preferably, dimethylsulfoxide. The reaction is run under an inert atmosphere such as argon or nitrogen. The reaction is run at a temperature in the range of about to 20° C. to about 50° C., more preferably, at room temperature. The resulting compound of formula V may be separated by conventional means such as crystallization or chromatography, or it may be used directly in the next step of a synthesis of this invention.

Procedure B

A compound of formula V may be reacted with an amine $R_5NR_6$ (wherein $R_5$ and $R_6$ are as described herein) to obtain a compound of formula VI. The reaction is run in a polar, aprotic, organic solvent such as acetonitrile, tetrahydrofuran, or more preferably, dimethylformamide, in the presence of a carbodiimide, such as dicyclohexylcarbodiimide, and in the further presence of an activating reagent such as N-hydroxysuccinimide, or more preferably 1-hydroxybenztriazole. The reaction is run at a temperature in the range of about 0° to about 50° C., more preferably, room temperature. The resulting compound of formula VI may be separated by conventional means such as crystallization or chromatography, or it may be used directly in the next step of the synthesis of this invention.

Amines of formula $R_5NR_6$ are known are may be prepared in accordance with known methods.

The next step of the synthesis is the deprotection of the blocked-$R_9$ group of a compound of formula VI to obtain a compound of formula I.

In the case of the tert-butoxycarbonyl (BOC) protecting group, the compound of formula VI may be converted to a final product of formula I of the invention by treatment with a mineral acid such as hydrochloric acid or sulfuric acid, or more preferably, the organic acid trifluoroacetic acid at a temperature in the range of about 0° C. to about 25° C., more preferably room temperature. The resulting mixture compound formula I of the invention may be separated by conventional means such as crystallization or chromatography.

In the case of the benzyloxycarbonyl (CBZ) protecting group, a compound of formula VI may be hydrogenolized by dissolving it in a solvent such as ethanol, or more preferably, methanol and 5% of 90% formic acid in the presence of a catalyst which facilitates hydrogenolysis such as palladium on carbon, or more preferably palladium black. After deprotection is complete, the palladium may be filtered and the filtrate evaporated under reduced pressure at 50° C. to obtain a compound of formula I of the invention. This compound of formula I may be further purified by conventional means such as crystallization or chromatography.

Compounds of formulas II and IV are known, may be prepared in accordance with known methods, or else they may be prepared as described herein.

FORMULA SCHEME 2

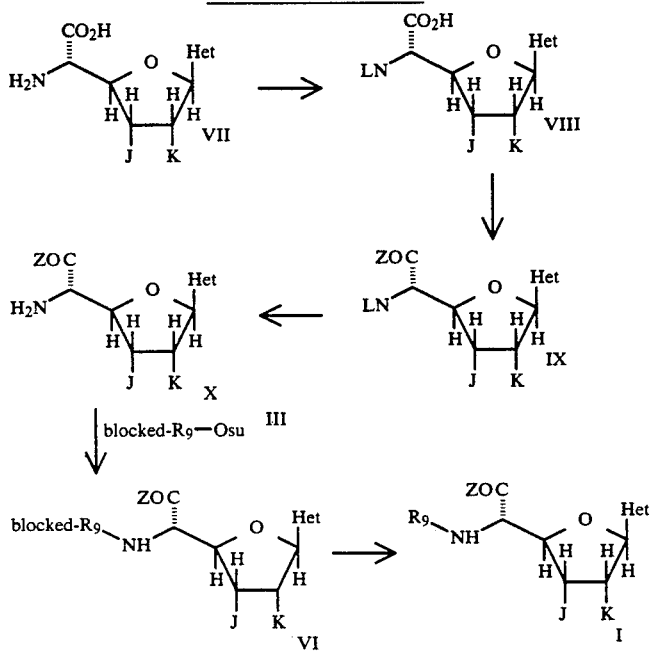

wherein $R_9$, Blocked-$R_9$, Het, J, K, and Z are as described above. L is a protecting group or a leaving group such as CBZ or BOC.

$(BOC)_2O$ denotes di-tert.butyldicarbonate.

Procedure C

A compound of formula VII may be reacted with di-tert.butyldicarbonate to obtain a compound of formula VIII. The solvent employed is a polar solvent such as methanol, N,N-dimethylformamide, or more preferably, water. The reaction is run at a pH in the range of about 8 to about 10, more preferably, 9.5. The reaction mixture is kept basic through use of an alkali metal carbonate such as sodium carbonate or potassium carbonate, or through use of an alkali metal hydroxide such as potassium hydroxide or, more preferably, sodium hydroxide. The reaction is run at a temperature in the range of about 0° to about 25° C., more preferably about room temperature.

The resulting compound of formula VIII may be separated by conventional means such as crystallization or chromatography, or it may be used directly in the next step of the synthesis of this invention.

A compound of formula VIII may be reacted with an amine $R_5NR_6$ (wherein $R_5$ and $R_6$ are as described herein) to obtain a compound of formula IX. The reaction is run in a polar organic solvent such as acetonitrile, tetrahydrofuran, or more preferably, dimethylformamide, in the presence of a carbodiimide, such as dicyclohexylcarbodiimide, and in the further presence of an activating reagent such as N-hydroxysuccinimide, or more preferably 1-hydroxybenztriazole. The reaction is run at a temperature in the range of about 0° to about 50° C., more preferably, room temperature. The resulting compound of formula IX may be separated by conventional means such as crystallization or chromatography, or it may be used directly in the next step of the synthesis of this invention.

Procedure D

A compound of formula IX may be converted to a compound of formula X by reaction in a mineral acid such as hydrochloric acid or sulfuric acid, or more preferably, the organic acid trifluoroacetic acid. The reaction is run at a temperature in the range of about 0° to about 25° C., more preferably room temperature. The resulting compound of formula X may be separated by conventional means such as crystallization or chromatography, or it may use directly in the next step of the synthesis of this invention.

A compound of formula X may be converted to a compound of formula VI by reaction with an active ester of a N-blocked-amino acid of the formula blocked-R$_9$—Osu     III wherein blocked-R$_9$, and Osu are as described herein. The reaction is run in an anhydrous polar organic solvent such as methyl sulfoxide, tetrahydrofuran, acetonitrile, or more preferably dimethylformamide, in the presence of a tertiary amine base such as diisopropylethylamine, N-methyl morpholine, or more preferably triethylamine at a temperature in the range of about 0° to about 50° C., or more preferably room temperature. The resulting compound of formula VI may be separated by conventional means such as crystallization or chromatography, or it may be used directly in the next step of the synthesis of this invention.

The next step of the synthesis is the deprotection of the blocked-R$_9$ group of a compound of formula VI to obtain a compound of formula I.

In the case of the tert.butoxycarbonyl (BOC) protecting group, the compound of formula VI may be converted to a final product of formula I of the invention by treatment with a mineral acid such as hydrochloric acid or sulfuric acid, or more preferably, the organic acid trifluoroacetic acid, at a temperature in the range of about 0° to about 25° C., more preferably room temperature. The resulting mixture compound formula I of the invention may be separated by conventional means such as crystalization or chromatography.

In the case of the benzyloxycarbonyl (CBZ) protecting group, a compound of formula VI may be hydrogenolized by dissolving it in a ethanol, or more preferably, 95% methanol and 5% formic acid in the presence of a catalyst which facilitates hydrogenolisis such as palladium on carbon, or more preferably palladium black. After deprotection is complete the palladium may be filtered and the filtrate evaporated under reduced pressure at 50° C. to obtain a compound of formula I of the invention. This compound of formula I may be further purified by conventional means such as crystallization or chromatography.

Compounds of formulas VII and III are known, may be prepared in accordance with known methods, or else they may be prepared as described herein.

The compounds of formula I of the invention are useful as agents for treating fungi.

TEST RESULTS

The minimum inhibitory concentrations (MIC-R and MIC-S) for a series of compounds of formula I of the invention are as shown in Table 1 below. The test results shown in the table were obtained from the test procedures set forth just below. MIC-R and MIC-S mean respectively, MICs taken against resistant and sensitive strains.

In vitro anti-fungal activity was determined in microtiter minimum inhibitory concentration (MIC) tests using Yeast Nitrogen Broth (YNB without amino acids, Difco., Detroit, Mich.) at pH 5.4. Yeasts were grown overnight in Sabouraud Dextrose Broth at 28° C. with shaking, and concentrations adjusted in sterile saline using a spectrophoptometer at 540 m$\mu$. Compounds were dissolved in various vehicles and diluted in media to twice the final concentrations. The Cetus Pro/Pette system was used to serially dilute 50 $\mu$l in round bottom 96 well plates (Falcon, Lincoln Park, N.J.). The turbidometrically adjusted yeast suspensions were diluted 1:3,000 in YNB. These dilutions when added to the wells, produced a final inoculum of $3 \times 10^3$/ml. Plates were incubated at 37° C. for 48 hours. MICs were defined as the lowest concentrations of compound that prevented visible growth. MICs were taken against the following organisms and expressed in the table above as the geometric mean. MIC-R and MIC-S mean respectively MICs against resistant and sensitive strains.

Resistant Strains

*Candida albicans* C79
*Candida albicans* C6
*Candida albicans* C8
*Candida albicans* C31
*Candida albicans* C54
*Candida albicans* C70
*Candida albicans* C104
*Candida albicans* C138
*Candida albicans* C140
*Candida stellatoidea* C45

Sensitive Strains

*Candida albicans* C141
Candida sp. C2
Candida sp. C109
*Candida parapsilosis* C67
*Candida tropicalis* C112
*Torulopsis glabrata* C95
*Candida pseudotropicalis* C 967
*Candida guillermondii* C137
Sacchararomyces C78
Sacchararomyces mutant C147

The mass spectrum molecular ion masses for these compounds (MS or Mass Spec) are also shown.

TABLE 1

Structure I: Core sugar ring with Z.OC-CH(NHR9)- substituent, O in ring, Het substituent, and two OH groups.

| No. | R9 | Z.OC | MIC-R | MIC-S | Mass Spec. |
|---|---|---|---|---|---|
| 1. | (CH3)2CH-CH(CH3)-CH(NH2)-CO (isoleucine-like) | CONH(CH2)11CH3 | 10 | 56 | 567 |
| 2. | CH3-S-CH2CH2-CH(NH2)-CO (methionine) | CONH(CH2)11CH3 | 24.3 | 29.9 | 585 |
| 3. | (CH3)2CH-CH(NH2)-CO (valine) | CONH(CH2)11CH3 | 17 | 26 | 553 |
| 4. | (CH3)2CH-CH2-CH(NH2)-CO (leucine) | CONH(CH2)11CH3 | 28 | 28 | 567 |
| 5. | (CH3)2CH-CH2-CH(NH2)-CO (leucine) | CONH(CH2)13CH3 | 181 | 111 | 595 |
| 6. | (CH3)2CH-CH2-CH(NH2)-CO (leucine) | CONH(CH2)9CH3 | 92 | 119 | 539 |
| 7. | CH3-S-CH2CH2-CH(NH2)-CO (methionine) | CH3O2C—(CH2)11—NHCO | >256 | >256 | 629 |
| 8. | CH3-S-CH2CH2-CH(NH2)-CO (methionine) | (CH2)12CH3NHCO | >128 | 13 | 599 |
| 9. | CH3-S-CH2CH2-CH(NH2)-CO (methionine) | HO2C—(CH2)11—NHCO | >256 | >256 | 615 |
| 10. | CH3-S-CH2CH2-CH(NH2)-CO (methionine) | CH3(CH2)8-CH(OH)-CH2-NHCO | 137 | 208 | 601 |
| 11. | Tryptophan residue (indol-3-yl-CH2-CH(NH2)-CO) | CONH(CH2)11CH3 | 11.3 | 69 | 640 |
| 12. | CH3-S-CH2CH2-CH(NH-Leu)-CO | CONH(CH2)11CH3 | 49 | 91 | 698 |

TABLE 1-continued
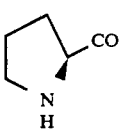
| No. | R₉ | Z.OC | MIC-R | MIC-S | Mass Spec. |
|---|---|---|---|---|---|
| 13. | 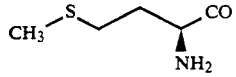 | CONH(CH₂)₁₁CH₃ | 74 | 119 | 551 |
| 14. | 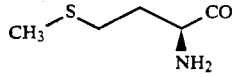 | CH₃CH₂—≡—(CH₂)₇—NHCO | 169 | 223 | 567 |
| 15. |  | 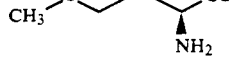(CH₂)₃—O—(CH₂)₆—NCO | >181 | >208 | 649 |
| 16. |  | CH₃—≡—(CH₂)₉—NCO | 169 | 208 | 581 |
| 17. | 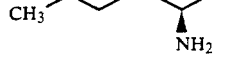 | CH₃CH₂CH₂—≡—(CH₂)₇—NCO | >223 | >169 | 584 |
| 18. | 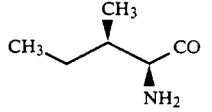 | CH₃CH₂ (CH₂)₈—NHCO | 89 | 49 | 583 |
| 19. | 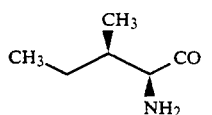 | CH₃(CH₂)₃ (CH₂)₆—NHCO | 64 | 104 | 565 |
| 20. |  | CONH(CH₂)₁₀CH₃ | 34 | 56 | 553 |
| 21. | 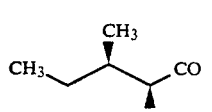 | CH₃CH₂ (CH₂)₈—NCO | 49 | 74 | 565 |
| 22. | 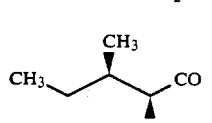 | CH₃ (CH₂)₉—NCO | 45 | 64 | 565 |
| 23. | 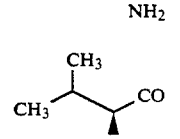 | CONH(CH₂)₁₁CH₃ | 52 | 111 | 567 |
| 24. | 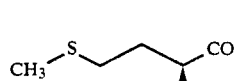 | CH₃S—(CH₂)₁₀—NHCO | 294 | 446 | 603 |

TABLE 1-continued

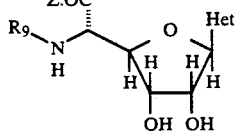

| No. | R9 | Z.OC | MIC-R | MIC-S | Mass Spec. |
|---|---|---|---|---|---|
| 25. | H2N-CO-CH2-CH2-CH(NH2)-CO- (glutamine side) | CONH(CH2)11CH3 | 181 | 223 | 582 |
| 26. | CH3-CH(NH2)-CO- | CONH(CH2)11CH3 | 74 | 338 | 525 |
| 27. | CH3-S-CH2-CH2-CH(NH2)-CO- | NC—(CH2)10—NHCO | >256 | >256 | 582 |
| 28. | CH3-S-CH2-CH2-CH(NH2)-CO- | HC(=O)NH—(CH2)10—NHCO | >256 | >256 | 600 |
| 29. | CH3-S-CH2-CH2-CH(NH2)-CO- | imidazol-1-yl—(CH2)10·NHCO | >256 | >256 | 624 |
| 30. | (CH3)2CH-CH(CH3)-CH(NH2)-CO- | CH3CH2-CH=CH-(CH2)10—NHCO (cis) |  |  | 593 |
| 31. | (CH3)2CH-CH(CH3)-CH(NH2)-CO- | CH3(CH2)11-CH(OH)-CH2-NHCO | 74 | >128 | 611 |
| 32. | (CH3)2CH-CH(CH3)-CH(NH2)-CO- | CH3S(CH2)10NHCO | >239 |  | 585 |
| 33. | (CH3)2CH-CH(CH3)-CH(NH2)-CO- | CH3(CH2)4-CH(CH2(CH2)3CH3)-NHCO |  |  | 567 |

In the above table Het is uracil for all compounds except compound no. 23 wherein Het is methyl-uracil which has the structure:

[structure of methyl-uracil: CH3-N attached to pyrimidine-2,4-dione with NH]

As can be seen from the above table, compounds of the invention exhibit anti-fungal activity against human and animal pathogens which are both sensitive to nikkomycins (MIC-S μg/ml<128) and resistant to nikkomycins (MIC-R μg/ml>2048).

In vivo anti-fungal activity was tested for in the following test protocol. Compounds of the invention were found to be active in the following test protocol.

MATERIALS AND METHODS

Vaginal Candida Infections in Hamsters

*C. albicans* (C60 or C79), clinical isolates, were grown on SDA slants for 48 hours at 28° C. Cells were washed off the slants with SDB broth to obtain a suspension of approximately $1 \times 10^8$ cells/ml. Groups of 10 female Syrian outbred hamsters (Charles River), weighing 100–120 grams, were used. On the first day of the experiment, the vagina was swabbed with a dry cotton swab to remove any mucus and to induce a slight irritation. The suspension of *C. albicans* (0.05 ml) was introduced into the vagina on three successive days using a syringe equipped with a blunt needle. Two days after infection, samples were obtained for culture by inserting a sterile cotton swab into the vagina. The swabs were placed into 10 ml of 0.9% saline containing cycloheximide (Actidione, Upjohn, 0.45 g/l) and chloramphenicol (Chloromycetin sodium succinate, Parke Davis, Morris Plains, N.J., 0.1 g/l), and then vigorously agitated to dislodge the vaginal sample. A 2 ml aliquot of each sample was then passed through a 0.45 micron Millipore filter. Following a saline rinse of the filters, the filters were placed onto mycosel agar plates and incubated at 37° C. After 48 h the number of *C. albicans* colonies on the filters were counted. Only animals that showed positive cultures were used for the experiments.

Treatment began 4 days after completion of infection. Compounds were solubilized in ethanol:PEG400: glycerol (10:45:45). Treatment was intravaginally at concentrations of 0.125-2% once daily for 4 days. Using cotton swabs, vaginal samples were obtained after 2, 4, 7 and 9 days of treatment and the swabs were processed as above. Efficacy was determined on the basis of negative cultures at each of the four time periods.

Materials and Methods

*C. albicans* Infection Studies in Mice ($PD_{50}$)

*C. albicans* Wisconsin (C 43) and *C. tropicalis* (C 112), grown on Sabouraud dextrose agar (SDA) slants for 48 h at 28° C., were suspended in saline and adjusted to 46% transmission at 550 nm on a spectrophotometer. The inoculum was further adjusted by hemacytometer and confirmed by plate counts to be approximately 1 or $5 \times 10^7$ CFU/ml. CF-1 mice (white, male, ca. 20 g, Harlan Sprague Dawley, Inc., Indianapolis, Ind.) were infected by injection 1 or $5 \times 10^6$ CFU into the tail vein. Antifungal agents were administered intravenously or subcutaneously in ethanol: water (10:90), 4 h post infection and once daily thereafter for 3 or 4 more days. Survival was monitored daily. The protective dose$_{50}$ ($PD_{50}$) was defined as that dose which allowed for 50% survival of mice.

The pharmaceutical compositions of the present invention may be formulated by combining a compound of the invention or pharmaceutically acceptable salt thereof with any suitable diluent, i.e., inert pharmaceutical carrier or diluent adapted for administration orally, parenterally, topically, vaginally or rectally.

Examples of suitable compositions include solid or liquid compositions for oral administration such as tablets, capsules, pills powders, granules, solutions, suspensions or emulsions. They may also be manufactured in the form of sterile solid compositions which can be dissolved in sterile water, physiological saline or some sterile injectable medium immediately before use.

Topical dosage forms may be prepared according to procedures well known in the art, and may contain a variety of ingredients, excipients, and additives. The formulations for topical use include ointments, creams, lotions, powders, aerosols, pessaries, and sprays. Of these, lotions, ointments, and creams, may contain water, oils fats, waxes, polyesters, alcohols or polyols, plus such other ingredients as fragrances, emulsifiers, and preservatives. Powders are made by mixing the active ingredient with a readily available, inert, pulverous distributing agent such as talcum, calcium carbonate, tricalcium phosphate, or boric acid. Aqueous suspensions of the above powders may also be made. Solutions or emulsions may also be prepared using inert solvents which are preferably nonflammable, odorless, colorless, and nontoxic, for example, vegetable oils, isopropanol, dimethyl sulfoxide, hydrogenated naphthalenes, and alkylated naphthalenes. Similarly, aerosol, and non aerosol sprays may be prepared using solutions or suspensions in appropriate solvents, for example, difluorodichloromethane for aerosols.

Parenteral forms to be injected intravenously, intramuscularly, or subcutaneously, are usually in the form of a sterile solution, and may contain salts or glucose to make the solution isotonic.

Compounds of the invention may also be incorporated in vaginal suppositories. Vaginal suppositories may be prepared by methods which are conventional in the art. In addition to comprising a compound of the invention, vaginal suppositories may contain a suppository base made up of biocompatible polymers, a surfactant, and an absorbent in a vegetable oil phase.

In addition, the vaginal suppositories may be further modified by inclusion of an antioxidant.

When used orally or parenterally, the compounds of the invention can be administered in an amount ranging from about 0.02 mg/kg body weight to about 40.0 mg/kg body weight, preferably from about 0.1 mg/kg body weight to about 20 mg/kg body weight per day.

Determination of the proper dosage of a compound of the invention for a particular situation is within the skill of the art. Generally, treatment is initiated with smaller dosages that are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of formula I and the pharmaceutically acceptable salts thereof will be regulated according to the judgment of the attending clinician considering such factors as age, condition and size of the patient as well as severity of the symptom being treated.

The invention disclosed herein is exemplified by the following preparative examples, which should not be construed to limit the scope of the disclosure. Alternative mechanistic pathways and analogous structures within the scope of the invention may be apparent to those skilled in the art.

EXAMPLE 1

Preparation of N-BOC-UPOC

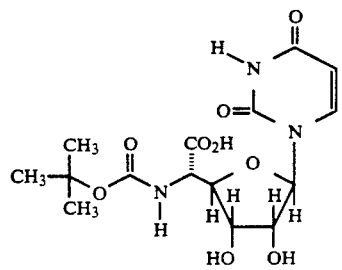

UPOC (8 g, 27.8 mmol) was dissolved in 200 ml of distilled water. The solution was stirred and the pH was adjusted to 9.5 with 20% sodium hydroxide solution. At room temperature di-tert. butyldicarbonate (8 g, 36.7 mmol) was added all at once and stirred while the pH was monitored at 9.5 with sodium hydroxide. After approximately 5 hours or after the reaction was complete by thin layer chromatography (tlc) (40% methanol-methylene chloride, normal phase silica plates) Dowex XFS-43279.00 hydrogen from resin was added to pH 3.0. The resin filtered off and the solvents were evaporated off under reduced vacuum at 45° C. The resulting solid was dissolved in 100 mL of methanol and added to stirring ether. The precipitate was filtered off and dried in a vacuum desiccator to obtain 10.5 g (97%) of the title product.

$^1$H-NMR (300 MHZ, CD$_3$OD) δ7.70 (1H, d, J=7.5 Hz), δ5.92 (1H, d, J=6 Hz), δ5.70 (1H, d, J=7.5 Hz), δ4.39 (1H, m,), δ4.32 (1H, m), δ4.23 (1H, m), δ4.12 (1H, t, J=5.25 Hz), δ1.45 (1H,s).

EXAMPLE 2

Preparation of N-BOC-6'-dodecylamido-UPOC

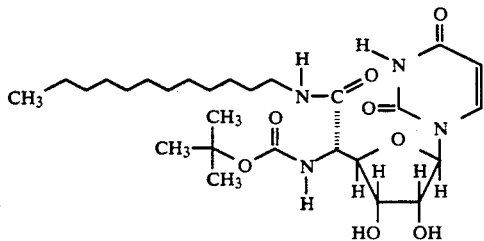

N-BOC-UPOC (5.2 g, 13.42 mmol) was dissolved in 150 ml of dry N,N-dimethylformamide (DMF). Dodecylamine (3.73 g, 20.13 mmol), dicyclohexylcarbodiimide (5.538 g, 26.84 mmol), and 1-hydroxybenztriazole (2.26 g, 16.77 mmol) were added and the resulting mixture was stirred at room temperature. After 48 hours, 2 ml of H$_2$O were added and the resulting mixture was stirred for 15 minutes. The precipitate was filtered off and the solvent, DMF, was evaporated under high vacuum at 50° C. to obtain an oil. The oil was chromatographed on silica gel using 1.25% to 5% methanol-methylene chloride to obtain 6.3 g (84%) of the title product.

EXAMPLE 3

6'-Dodecylamido-UPOC-trifluoroacetate

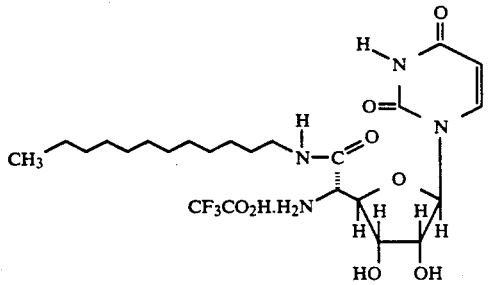

N-BOC-6'-dodecylamido-UPOC (6.25 g, 11.25 mmol) was dissolved in 15 ml of trifluoroacetic acid and the resulting mixture was stirred at room temperature for 5 minutes. 100 ml of ether were added and the solids were filtered off to obtain 6.01 g of title product after drying in a vacuum desiccator.

$^1$H-NMR (300 MHZ, D$_2$O) δ7.62 (1H, d, J=8.07 Hz), 5.66 (1H, d, J=8.01 Hz), 5.49 (1H, d, J=8.87 Hz) 4.28 to 4.34 (2H, m), 4.16 (1H, t, J=4.95 Hz), 4.08 (1H, d, J=5.22 Hz), 1.46 (2H, m), 1.22 (20H, br.s), 0.835 (3H,t, J=6.99 Hz).

EXAMPLE 4

Preparation of 6'-Dodecylamido-5-N-L-Valinyl-UPOC

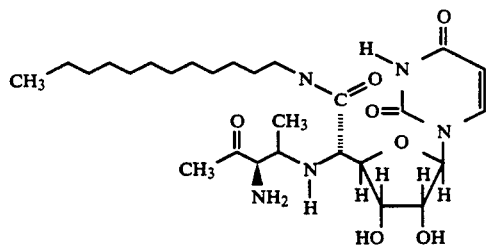

6'-Dodecyamido-UPOC trifluoroacetic acid salt (0.100 g, 0.176 mmol) was dissolved in 1.76 ml of dimethylformamide (DMF). Triethylamine (0.024 ml, 0.176 mmol) followed by N-oxysuccinimide ester of N-L-BOC Valine (0.110 g, 0.352 mmol) were added and the resulting mixture was stirred at room temperature. After 24 hours, the DMF was evaporated under high vacuum at 50° C. to obtain a semi-solid. The semi-solid was chromatographed on silica gel as described above to obtain 0.12 g (80%) which were dissolved in approximately 1 ml of trifluoroacetic acid for 5 minutes. Diethyl ether (20 ml) was added and the precipitate was filtered off to give 0.12 g of title product.

FABMS 554 (M+1).

EXAMPLE 5

Preparation of 2-S-N-BOC-amino-3-R-methyl-pentenoic acid

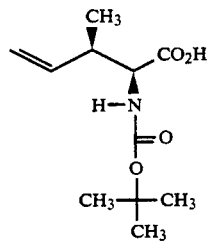

For the preparation of the racemic mixture of the formula just above, see P. A. Bartlett and J. F. Barstow, J. Org. Chem. 47, 3933–3941 (1982). 2-R,S-N-BOC-amino-3-R,S-methyl-pentenoic acid was resolved into its 2-S configuration as follows: To stirring trifluoroacetic acid (75 ml) was added 2-R,S-N-BOC-amino-3-R,S-methyl-pentenoic acid (25.79 g) portionwise. The mixture was stirred until dissolved. 200 ml of diethyl ether was slowly added to obtain 21.63 g after drying. The solid was dissolved in 250 ml of distilled water and cooled in an ice bath. The pH was adjusted to 9-9.5 with 25% NaOH. Acetic anhydride (25 ml) was dripped in while maintaining the pH at 9-9.5 with 25% NaOH. After thin layer chromatography (tlc) indicated completion of reaction, concentrated hydrochloric acid was added until the pH=2.0. The mixture was extracted with 4×200 ml of ethyl acetate, dried over magnesium sulfate, filtered, and evaporated to obtain 14.8 g of an oil. The oil of 2-R,S-N-acetyl-3-R,S-methyl-pentenoic acid was dissolved in 1 L of water. The pH was adjusted to 7.9 with 2N LiOH. Acylase I was mixture was stirred for 1 hour. The mixture was then allowed to stand at 37° C. for 72 hours. The pH was adjusted to 4.9 with acetic acid, charcoal was added, and the resulting mixture was stirred for 1 hour. The mixture was filtered on a celite pad, added to a 500 ml column of XFS-43279.00 resin in the hydrogen form, and washed with 2 l of distilled water. The compound was eluted with ammonium hydroxide (50 ml of 30% diluted to 1 l of water). The column was monitored by tlc. The eluent containing the product was concentrated to obtain 4.97 g of title product after drying. H[1]-NMR, M.S., and CHN identical to the unresolved product reported in the Bartlett paper. Preparation of 2-S-N-BOC-allo-isoleucine in the example just below confirmed that S conformation of the title product of the present example.

EXAMPLE 6

Preparation of 2-S-N-BOC-allo-isoleucine

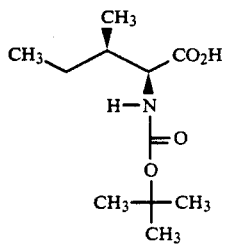

2-S-N-BOC-amino-3-methyl-C-allyl glycine (1 g) was hydrogenated in ethylacetate using 50 mg of 10% palladium on carbon at 50 psi of hydrogen for 1 hour. The solids were filtered off and evaporated to obtain the title product. H[1]-NMR, M.S., and CHN identical to known N-BOC-isoleucine.

PREPARATION OF ALKYL AMINES AND SUBSTITUTED AMINES

EXAMPLE 7

Preparation of 2-hydroxy-dodecylamine

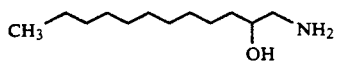

1-dodecene (16.8 g, 0.1 mmol) was dissolved in 400 ml of methylene chloride and cooled in an ice bath to 0°. 20 g of m-chloroperbenzoic acid were added and the reaction mixture was stirred at room temperature for 18 hours. The mixture was washed with a sodium bisulfite solution followed by sodium bicarbonate followed by water. The methylene chloride layer was dried over magnesium sulfate, filtered, and evaporated to dryness to obtain the epoxide. The epoxide (2.85 g) was dissolved in 120 ml of N,N-dimethylformamide and phthalimide (6.6 g) and cesium carbonate (4.89 g) were added. The reaction mixture was stirred under a nitrogen atmosphere for 18 hours at 80°. The solution was allowed to cool to room temperature. The solids were filtered off and washed with 20% ethyl acetate/hexanes. The mixture was evaporated to obtain a solid residue and chromatographed on a silica gel column using 20% ethyl acetate/hexanes as the eluent to obtain 4.24 gm of 2-hydroxy-1-phthalimido dodecane. The 4.24 g were dissolved in 100 ml of absolute ethanol. 1.2 ml of hydrazine hydrate were added and the mixture was heated on a steam bath for 4 hours. The precipitate was filtered off and evaporated to obtain an oily residue which was chromatographed on a silica gel column using 10% methanol/methylene chloride to obtain 2.3 g of the title product. $^1$H-NMR (200 MHZ, CD$_3$OD) δ0.93 (3H, t, J=6 Hz), 1.2–1.55(18H, m), 1.7(2H, bs, exchangeable protons), 2.55 (1H, dd, J=10 and 6.8 Hz), 2.89 (1H, J=10 and 4 Hz)3.45–3.6 (1H, m)

EXAMPLE 8

Preparation of 10-thiomethyl-1-aminodecane

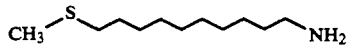

10-bromo-1-phthalimidodecane (3.97 g, 10 mmol) was dissolved in 40 ml of N,N-dimethylformamide and 0.8 g of sodium thiomethoxide was added. The reaction mixture was heated and stirred for 2 hours at 80° C. The reaction mixture was allowed to cool to room temperature and was added to brine and extracted with ethylacetate. The product crystallized from hexane to give 3.75 g of the phthalimido compound which was treated with 1.5 ml of hydrazine hydrate in 100 ml of ethyl alcohol at steam bath temperature for 1 hour. The reaction mixture was allowed to cool to room temperature, the solids were filtered off and the solvent was evaporated to obtain a gummy solid. The gummy solid was chromatographed on a silica gel column using 5% methanol/methylene chloride as the eluent to obtain 1.7 g of title product.

$^1$H-NMR (200 MHZ, CD$_3$OD) δ1.25 (12H, bs), 1.45–1.65(4H, m), 2.5(2H, t, J=6 Hz), 2.78(2H, t, J=6 Hz), 5.02(2H, bs, exchangeable)

EXAMPLE 9

Preparation of 10-(1H-1,2,4-triazolyl)-1-aminodecane

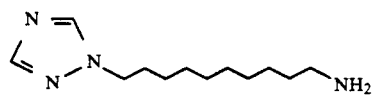

The procedure for the preparation of 10-thiomethyl-1-aminodecane was followed except sodium 1,2,4-triazole was used Instead of sodium thiomethoxide to obtain the title product in 75% yield.

$^1$H-NMR (200 MHZ, CD$_3$OD) δ1.29 (12H, bs), 1.47(2H, t, J=6.69 Hz), 1.84–1.88(2H, m), 2.65(2H, t, 6.9 Hz), 4.22(2H, t, J=6.9 Hz), 7.98(1H,s), 8.46(1H, s)

EXAMPLE 10

Preparation of 10-cyano-1-aminodecane

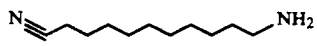

The procedure for the preparation of 10-thiomethyl-1-aminodecane was followed except potassium cyanide was used with 18-crown-6 as a catalyst instead of sodium thiomethoxide to obtain the title product in 80% yield.

$^1$H-NMR (200 MHZ, CD$_3$OD) δ1.3(12H, bs), 1.45(2H m), 1.59–1.71(2H, m), 2.35(2H, t, J=6.9 Hz), 2.71(2H, t, J=6.9 Hz)

EXAMPLE 11

Preparation of 1-amino-10-formamido-decane

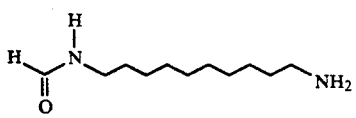

1,10-diaminodecane (6.88 g, 40 mmol) were dissolved in 100 ml of ethanol and 3.22 ml of ethylformate was added. The reaction mixture was stirred at room temperature under a nitrogen atmosphere for 18 hours and evaporated to dryness. The residue was chromatographed on a silica gel column using 25% methanol/methylenechloride as the eluent to obtain 4 g of the title product.

$^1$H-NMR (200 MHZ, CD$_3$OD) δ1.32(12H, bs), 1.4–1.6(2H, m), 2.62(2H, t, J=7.41 Hz), 3.20(2H, t, J=7.41 Hz), 3.3–3.4 (2H,m), 8.02 (1H,s)

EXAMPLE 12

Preparation of O-benzyl-dodecylhydroxylamine

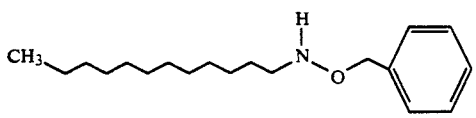

O-benzyl-hydroxylamine (8.63 g, 54 mmol) was dissolved in 200 ml of ethanol and 3 ml of water. Dodecanal (10 g, 54 mmol) was added and the mixture was stirred at room temperature for 4 hours. The mixture was evaporated to dryness under vacuum and dissolved in 200 ml of ethyl acetate. The ethyl acetate solution was washed with water followed by saturated sodium bicarbonate solution. The ethyl acetate layer was dried over magnesium sulfate, filtered, and evaporated to obtain a clear oil. The oil was chromatographed on a silica gel column using 5% ethyl acetate/hexanes as the eluent to obtain 12.5 g (80%) of the intermediate O-benzyl-dodecylhydroxylimine. The imine (5.76 g, 20 mmol) was dissolved in 50 ml of tetrahydrofuran and cooled under a nitrogen atmosphere in an ice bath. Borane-tetrahydrofuran (34 ml) was dripped in and the mixture was stirred for 4 hours at ice bath temperature. The tetrahydrofuran was evaporated off to obtain a clear oil. The mixture was cooled in an ice bath and a few drops of 10% sodium hydroxide were added carefully so as to avoid excessive foaming. After the reaction subsided a total of 10 ml of 10% sodium hydroxide was added and the mixture was refluxed for 1 hour. The mixture was chromatographed on a silica gel column using 10% ethyl acetate/hexanes to obtain 0.67 g of title compound.

$^1$H-NMR (200 MHZ, CDCl$_3$) δ0.9 (3H, t, J=6 Hz), 1.2–1.35 (20H, m), 1.5–1.65(2H, m), 2.7–2.9 (2H,m), 4.68(2H, s), 7.3–7.5 (5H, m)

PREPARATION OF UNSATURATED ALKYL AMINES AND RELATED AMINES AND PRODUCTS

EXAMPLE 13

9-Dodecyn-1-amine

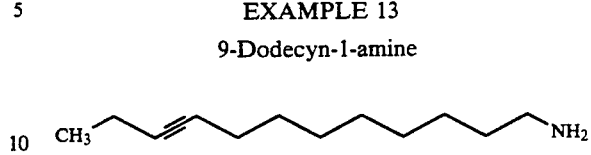

a) Triethylamine (4.3 ml) was added to a solution of 9-dodecyn-1-ol (5.1 g, 28 mmol) in 50 ml CH$_2$Cl$_2$, and the mixture was then added dropwise at 0° C. to a solution of methanesulfonyl chloride (2,2 ml, 28 mmol) in 10 ml CH$_2$Cl$_2$. The mixture was stirred another 4 hours at room temperature, then cooled to 0°–5° C. The solution was washed with cold 5% aqueous sodium bicarbonate, cold 1N HCl, cold water, then saturated brine. The extract was dried over Na$_2$SO$_4$ and filtered and evaporated. The solvent was evaporated to leave crude 1-(9-dodecynyl) methanesulfonate.

c) The crude 9-dodecynylazide from example 13b (5.8 g, 28 mmol) was dissolved in 120 ml THF, triphenylphosphine (7.7 g, 29 mmol) was added in portions. The mixture was stirred at room temperature for 2 hours. Water was added (0.7 ml, 39 mmol) and the mixture was stirred 18 hours. The mixture was concentrated to a sludge, diluted with hexanes, and suction-filtered. The filtrate was washed with MeOH-water (3:7), and evaporated. The residue was dissolved in 0.5N HCl, and washed with Et$_2$O. 6N NaOH was added to adjust the mixture to pH 6. The mixture was washed with Et$_2$O again, 6N NaOH was added to adjust the mixture to pH 10. The product was extracted with Et$_2$O. 28 ml of 1M HCl-dioxane solution was added and the mixture was evaporated to leave 9-dodecyn-1-amine hydrochloride (4.0 g, 66% yield overall): C$_{12}$H$_{23}$N•HCL (217.78); $^1$H-NMR (CDCl$_3$) δ8.3 (br s,3), 2.96 (m,2), 2.11 (m,4), 1.72 (m,2), 1.5–1.2 (m,10), 1.08 (t,3). Anal. calcd.: theory: C, 66.18; H, 11.11; N, 6.43. Found: C, 66.76; H, 10.63; N, 6.32.

EXAMPLE 14

10-Dodecyn-1-aminehydrochloride

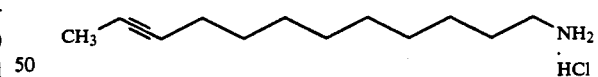

The procedure of example 13 a.–c. was followed but 10-dodecyn-1-ol was substituted in place of 9-dodecyn-1-ol to obtain the title compound (65% yield): C$_{12}$H$_{23}$N•HCL (217.78); $^1$H-NMR (CD$_3$OD) δ2.91 (t,2), 2.09 (m,2), 1.71 (t,3), 1.65 (m,2), 1.5–1.3 (m, 12). Anal. calcd.: theory: C, 66.18; H, 11.11; N, 6.43. Found: C, 66.18; H, 10.63; N, 6.22.

EXAMPLE 15

(Z)-7-Dodecen-1-amine

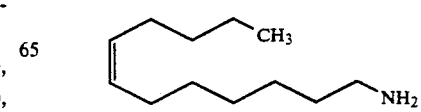

The procedure of example 13a.-c. was followed but (Z)-7-dodecen-1-ol was substituted in place of 9-dodecyn-1-ol to obtain the hydrochloride salt of the title compound. This compound was dissolved in 0.5N NaOH and extracted with Et$_2$O. The extract was dried over Na$_2$SO$_4$ and filtered. The solvent was evaporated to leave the title compound as an oil (36% yield): C$_{12}$H$_{25}$N (183.34); $^1$H-NMR (CDCl$_3$) δ5.36 (m,2), 2.69 (t,2), 2.02 (m,4), 1.45 (m,2), 1.3 (m,10), 0.90 (t,3).

EXAMPLE 16

(Z)-11-Tetradecen-1-aminehydrochloride

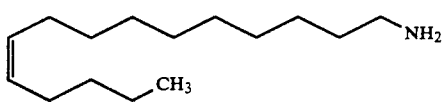

The procedure of example 13a.-c. was followed but (Z)-11-tetradecen-1-ol was substituted in place of 9-dodecyn-1-ol to obtain the title compound (31% yield): C$_{14}$H$_{29}$N•HCL (247.85); $^1$H-NMR (CDCl$_3$) δ8.3 (br s,3), 5.32 (m,2), 2.98 (m,2), 2.1-1.9 (m,4), 1.78 (m,2), 2.5-2.2 (m,14), 0.96 (t,3). Anal. calcd: C, 67.84; H, 12.20; N, 5.65; found: C, 66.57; H, 11.93; N, 5.69; calcd. for C$_{14}$H$_{29}$N•HCL•¼H$_2$O: C, 66.63; H, 12.18; N, 5.50.

EXAMPLE 17

(E)-10-Dodecen-1-aminehydrochloride

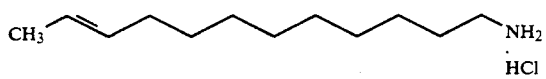

10-Dodecyn-1-amine hydrochloride (2.0 g, 9.2 mmol) and 1 ml THF were added to 30 ml diglyme. Lithium aluminum hydride (2 g, 53 mmol) were added and the mixture was heated at 150° C. for 96 hours. The mixture was cooled and 15% aqueous NaOH was added and the mixture was extracted with Et$_2$O. The extracts were dried over Na$_2$SO$_4$, filtered, and the solvent was evaporated. The residue was chromatographed on silica gel eluting with CH$_2$Cl$_2$-MeOH-NH$_4$OH (150:90:1) to obtain an oil. The oil was dissolved in Et$_2$O, 9 ml 1N HCl-dioxane solution were added, and solvent was evaporated to leave the title compound (0.9 g, 45% yield): C$_{12}$H$_{25}$N•HCl (219.80); $^1$H-NMR (CDCl$_3$) δ8.3 (br s,3), 5.41 (m,2), 2.99 (m,2), 1.97 (m,2), 1.8 (m,2), 1.64 (d,3), 1.4-1.2 (m,12). Anal. calcd.: C, 65.57; H, 11.92; N, 6.37; found: C, 65.56; H, 11.55; N, 6.15.

EXAMPLE 18

(E)-9-Dodecen-1-aminehydrochloride

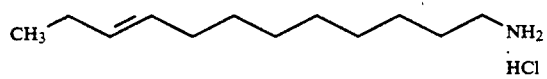

The procedure of example 17 was followed but 9-dodecyn-1-amine hydrochloride was substituted in place of 10-dodecyn-1-aminee hydrochloride to obtain the title compound (59% yield): C$_{12}$H$_{25}$N•HCl (219.80); $^1$H-NMR (CDCl$_3$) δ8.3 (br s,3), 5.40 (m,2), 2.99 (m,2), 1.98 (m,4), 1.78 (m,2), 1.5-1.3 (m,10); 0.97 (t,3).

EXAMPLE 19

7-Oxa-11-phenylundecylaminehydrochloride

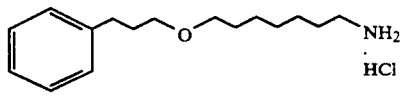

The procedure of example 13b. and 13c. was followed but 7-oxa-11-phenylundecylbromide was substituted in place of crude 1-(9-dodecynyl) methanesulfonate to obtain the title compound (46% yield): C$_{16}$H$_{27}$NO•HCl (285.86); $^1$H-NMR (CDCl$_3$) δ8.3 (br s,3), 7.3-7.1 (m,5), 3.37 (q,4), 3.00 (br s,2), 2.62 (t,2), 1.9-1.5 (m,8), 1.4 (br s,4).

EXAMPLE 20

(2-(Pentyl)heptylamine

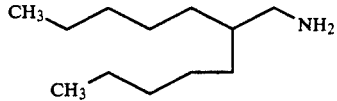

Sodium borohydride (0.55 g, 14.6 mmol) was added to a solution of 6-undecanone (1.66 g, 9.8 mmol) in 50 ml methanol, and the mixture was stirred at room temperature 2 hours. Solvent was evaporated and water was added to the residue which was extracted with CH$_2$Cl$_2$. The extracts were dried over anhydrous potassium carbonate, filtered, and the solvent was evaporated to leave crude 6-undecanol. The procedure of example 13 a. was followed but the crude 6-undecanol was substituted in place of 9-dodecyn-1-ol to obtain crude 6-undecanyl methanesulfonate. The crude 6-undecanyl methanesulfonate was dissolved in 20 ml acetonitrile and 1 g potassium cyanide were added, as well as 50 mg 18-crown-6, and 100 mg Et$_4$NCN. The mixture was stirred and heated at reflux for 4 days. The mixture was cooled, poured into 5% aqueous NaOH, and extracted with CH$_2$Cl$_2$. The extracts were dried over Na$_2$SO$_4$. The extracts were filtered, and the solvent was evaporated. The residue was chromatographed on silica gel eluting with EtOAc-hexanes (2:98) to obtain crude 3-pentylheptanenitrile in low yield. This nitrile was dissolved in 30 ml THF, 1 ml 1M BH$_3$-THF solution was added, and the mixture was stirred at reflux for 4 hours. Water and 1N NaOH were added. The mixture was concentrated and water was added. The mixture was extracted with CH$_2$Cl$_2$. The extracts were dried over Na$_2$SO$_4$, filtered, and the solvent was evaporated to leave the title compound as an oil (57 mg, 3% yield overall): C$_{12}$H$_{27}$N (185.36); $^1$H-NMR (CDCl$_3$) δ2.64 (d,2), 1.28 (m,17), 0.89 (t,6).

EXAMPLE 21

N-(Z-9-dodecenyl)-L-methioninyl-UPOC amide

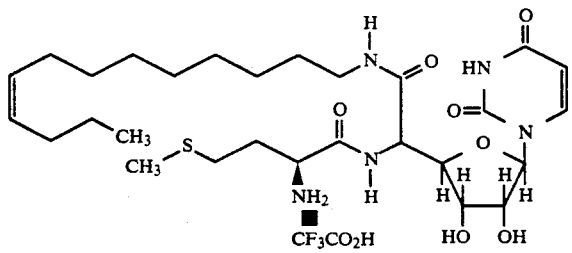

N-(Z-9-dodecynyl)-L-methioninyl-UPOC amide (47 mg, 0.068 mmol) were added to 1 mg $PdCl_2$ to 10 ml DMF, and the mixture was hydrogenated at 2.5 atm. for 0.5 hour. The mixture was filtered and the solvent was evaporated. The residue was chromatographed on $C_{18}$ reverse-phase silica eluting with MeOH-water-trifluoroacetic acid (75:25:0.1) to obtain the title compound (12.5 mg, 26% yield): $C_{27}H_{45}N_5O_7S \bullet CF_3COOH$ (697.77); $H^1$-NMR ($CD_3OD$) $\delta$7.59 (d,1), 5.64 (d,1), 5.58 (d,1), 5.31 (m,2), 4.57 (d,1), 4.38 (t,1), 4.10 (t,1), 4.01 (m,1), 3.94 (t,1), 3.20–3.05 (m,2), 2.49 (t,2), 2.03(s,3), 1.9 (m,4), 1.4–1.2 (m,14), 0.81 (m,3).

The following table illustrates how other compounds of formula I of the invention may be made by using procedures analogous to those set forth above.

| No. | $R_9CO$ | Z.OC | Starting Materials | Process |
|-----|---------|------|--------------------|---------| 
| 1. | (CH3)2CH-CH(NH2)-CO (alloisoleucine) | $CONH(CH_2)_{11}CH_3$ | Use N-BOC-alloisoleucine in procedure D | C/D |
| 2. | $CH_3$-S-CH2CH2-CH(NH2)-CO | $CONH(CH_2)_{11}CH_3$ | Use N-L-BOC-methionine in procedure D | C/D |
| 3. | (CH3)2CH-CH(NH2)-CO (valine) | $CONH(CH_2)_{11}CH_3$ | Use N-Boc-L-valine in procedure D | C/D |
| 4. | (CH3)2CH-CH(NH2)-CO (isoleucine) | $CONH(CH_2)_{11}CH_3$ | Use N-BOC-isoleucine in procedure D | C/D |
| 5. | alloisoleucine | $CONH(CH_2)_{13}CH_3$ | Use N-BOC-alloisoleucine in procedure A. Use tetradecylamine in procedure B | A/B |
| 6. | alloisoleucine | $CONH(CH_2)_9CH_3$ | Use N-BOC-alloisoleucine in procedure A. Use decylamine in procedure B | A/B |
| 7. | $CH_3$-S-CH2CH2-CH(NH2)-CO | $CH_3O_2C-(CH_2)_{11}-NHCO$ | Use N-BOC-L-methionine in procedure A. Use carboxymethyl undecylamine in procedure B | A/B |
| 8. | $CH_3$-S-CH2CH2-CH(NH2)-CO | $CONH(CH_2)_{12}CH_3$ | Use N-BOC-L-methionine in procedure A. Use tridecylamine in procedure B. | A/B |
| 9. | $CH_3$-S-CH2CH2-CH(NH2)-CO | $HO_2C-(CH_2)_{11}-NHCO$ | Use N-BOC-L-methionine in procedure A. Use 12-aminododecanoic acid in procedure B | A/B |

-continued

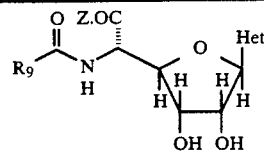

| No. | R₉CO | Z.OC | Starting Materials | Process |
|---|---|---|---|---|
| 10. | CH₃-S-CH₂CH₂-CH(NH₂)-CO | CH₃(CH₂)₉-CH(OH)-CH₂-NHCO | Use N-BOC-L-methionine in procedure A. Use 2-hydroxydodecylamine in procedure B | A/B |
| 11. | (indol-3-yl)-CH₂-CH(NH₂)-CO | CONH(CH₂)₁₁CH₃ | Use N-BOC-L-tryptophan in procedure D | C/D |
| 12. | CH₃-S-CH₂CH₂-CH(NH-Leu)-CO | CONH(CH₂)₁₁CH₃ | Use N-BOC-L-Leucine-L-Methionine in procedure D | C/D |
| 13. | (prolyl)-CO | CONH(CH₂)₁₁CH₃ | Use N-BOC-L-proline in procedure D | C/D |
| 14. | CH₃-S-CH₂CH₂-CH(NH₂)-CO | CH₃CH₂-C≡C-(CH₂)₇-NHCO | Use N-BOC-L-methionine in procedure A. Use 1-amino-8-undecyne in procedure B | A/B |
| 15. | CH₃-S-CH₂CH₂-CH(NH₂)-CO | C₆H₅-(CH₂)₃-O-(CH₂)₆-NCO | Use N-BOC-L-methionine in procedure A. Use 1-amino-8-undecyne in procedure B | A/B |
| 16. | CH₃-S-CH₂CH₂-CH(NH₂)-CO | CH₃-C≡C-(CH₂)₉-NCO | Use N-BOC-L-methionine in procedure A. Use 7-oxa-11-phenyl undecylamine in procedure B | A/B |
| 17. | CH₃-S-CH₂CH₂-CH(NH₂)-CO | CH₃(CH₂)₂-C≡C-(CH₂)₇-NCO | Use N-BOC-L-methionine in procedure A. Use 1-amino-8-dodecyne in procedure B | A/B |
| 18. | CH₃-S-CH₂CH₂-CH(NH₂)-CO | CH₃CH₂-CH=CH-(CH₂)₈-NHCO | Use N-BOC-L-methionine in procedure A. Use 1-amino-9-dodecyne in procedure B | A/B |
| 19. | CH₃-CH₂-CH(CH₃)-CH(NH₂)-CO | CONH(CH₂)₁₀CH₃ | Use N-BOC-alloisoleucine in procedure A. Use 1-amino-7-dodecene in procedure B | A/B |
| 20. | CH₃-CH₂-CH(CH₃)-CH(NH₂)-CO | CONH(CH₂)₁₀CH₃ | Use N-BOC-alloisoleucine in procedure A. Use undecylamine in procedure B | A/B |
| 21. | CH₃-CH₂-CH(CH₃)-CH(NH₂)-CO | CH₃CH₂-CH=CH-(CH₂)₈-NCO | Use N-BOC-alloisoleucine in procedure A. Use 1-amino-9-dodecene in procedure B | A/B |

-continued

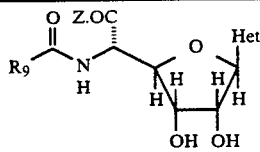

| No. | R$_9$CO | Z.OC | Starting Materials | Process |
|---|---|---|---|---|
| 22. | (CH$_3$)$_2$CH-CH(CH$_3$)-C(NH$_2$)-CO | CH$_3$-CH=CH-(CH$_2$)$_9$-NCO | Use N-BOC-alloisoleucine in procedure A. Use 1-amino-10-dodecene in procedure B | A/B |
| 23. | (CH$_3$)$_2$CH-C(NH$_2$)-CO | CONH(CH$_2$)$_{11}$CH$_3$ | Use N-BOC-L-valine in procedure D | C/D |
| 24. | CH$_3$S-(CH$_2$)$_2$-C(NH$_2$)-CO | CH$_3$S-(CH$_2$)$_{10}$-NHCO | Use N-BOC-L-methionine in procedure A. Use 10-thiomethyldecylamine in procedure B | A/B |
| 25. | H$_2$N-CO-(CH$_2$)$_2$-C(NH$_2$)-CO | CONH(CH$_2$)$_{11}$CH$_3$ | Use N-BOC-L-glutamine in procedure D | C/D |
| 26. | CH$_3$-C(NH$_2$)-CO | CONH(CH$_2$)$_{11}$CH$_3$ | Use N-BOC-L-alanine in procedure D | C/D |
| 27. | CH$_3$S-(CH$_2$)$_2$-C(NH$_2$)-CO | NC-(CH$_2$)$_{10}$-NHCO | Use N-BOC-L-methionine in procedure A. Use 10-nitrile decylamine in procedure B | A/B |
| 28. | CH$_3$S-(CH$_2$)$_2$-C(NH$_2$)-CO | CHO-NH-(CH$_2$)$_{10}$-NHCO | Use N-BOC-L-methionine in procedure A. Use 1-amino-10-formylamido in procedure B | A/B |
| 29. | CH$_3$S-(CH$_2$)$_2$-C(NH$_2$)-CO | triazolyl-N-(CH$_2$)$_{10}$·NHCO | Use N-BOC-L-methionine in procedure A. Use 10-(1H-triazolyl)-decyl-amine in procedure B | A/B |
| 30. | (CH$_3$)$_2$CH-CH(CH$_3$)-C(NH$_2$)-CO | CH$_3$CH$_2$-CH=CH-(CH$_2$)$_{10}$-NHCO | Use N-BOC-L-isoleucine in procedure A. Use 11-tetradeceneamine in procedure B | A/B |
| 31. | (CH$_3$)$_2$CH-CH(CH$_3$)-C(NH$_2$)-CO | CH$_3$(CH$_2$)$_{11}$-CH(OH)-CH$_2$-NHCO | Use N-BOC-alloisoleucine in procedure A. Use 2-hydroxytetradecylamine in procedure B | A/B |
| 32. | (CH$_3$)$_2$CH-CH(CH$_3$)-C(NH$_2$)-CO | CH$_3$S(CH$_2$)$_{10}$NHCO | Use N-BOC-alloisoleucine in procedure A. Use 10-thiomethyldecylamine in procedure B | A/B |
| 33. | (CH$_3$)$_2$CH-CH(CH$_3$)-C(NH$_2$)-CO | CH(CH$_2$(CH$_2$)$_4$CH$_3$)$_2$-NHCO | Use N-BOC-alloisoleucine in procedure A. Use 2-pentylheptylamine in procedure B | A/B |

Het in the above table is uracil for all compounds except compound no. 23 where it is methyl-uracil, that is

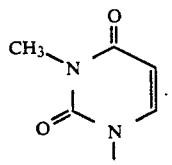

What is claimed is:

1. A compound of the formula:

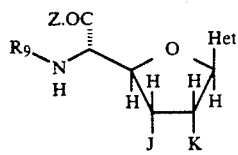

or a pharmaceutically acceptable salt thereof wherein:
Het is

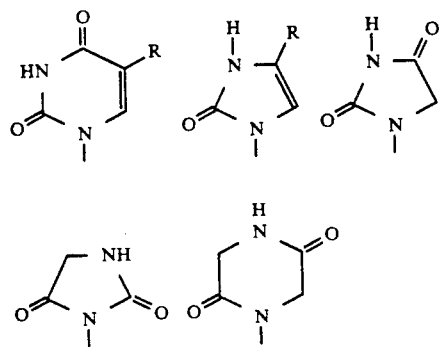

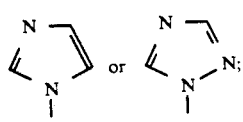

R is H; COOH; $C_1$-$C_{12}$ alkyl; CHO; CN; $CH_2OH$; or $CONH_2$;

$R_9$ is a natural amino acid substituted at the 2-amino position by H, a natural amino acid, or a metabolizable group;

J and K are the same or different and are independently selected from the group consisting of OH, H, Br, Cl and F;

and COZ is $CONH(CH_2)_{11}CH_3$.

2. A compound according to claim 1 wherein Het is uracil.

3. A compound according to claim 1 wherein $R_9$ is a natural amino acid in the L configuration.

4. A compound according to claim 1, wherein J and K are both OH.

5. A compound, selected from the group consisting of

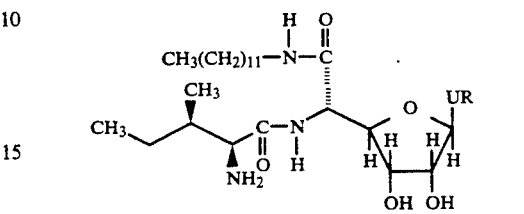

and

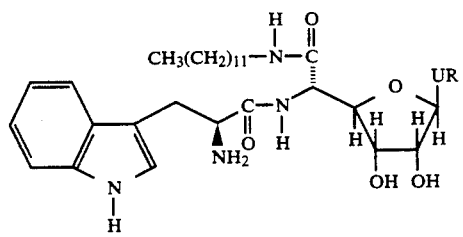

or a pharmaceutically acceptable salt thereof.

6. The compound

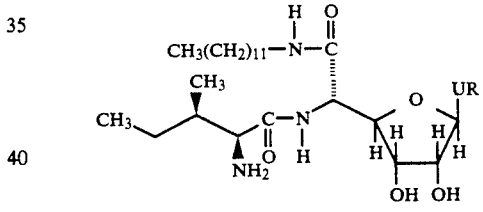

or a pharmaceutically acceptable salt thereof.

7. A compound selected from the group consisting of

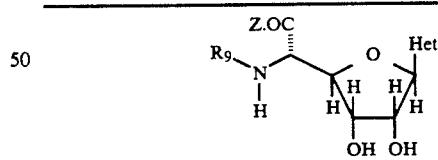

| No. | $R_9$ | Z.OC | Het |
|---|---|---|---|
| 1. | | $CONH(CH_2)_{11}CH_3$ | UR |
| 2. | | $CONH(CH_2)_{11}CH_3$ | UR |

-continued

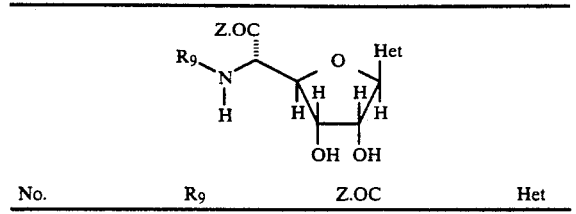

| No. | R9 | Z.OC | Het |
|---|---|---|---|
| 3. | (CH3)2CH-CH(NH2)-CO | CONH(CH2)11CH3 | UR |
| 4. | CH3-CH2-CH(CH3)-CH(NH2)-CO | CONH(CH2)11CH3 | UR |
| 11. | Trp (indolyl-CH2-CH(NH2)-CO) | CONH(CH2)11CH3 | UR |
| 12. | CH3-S-CH2-CH2-CH(NH-Leu)-CO | CONH(CH2)11CH3 | UR |
| 13. | Pro (pyrrolidine-2-CO) | CONH(CH2)11CH3 | UR |

-continued

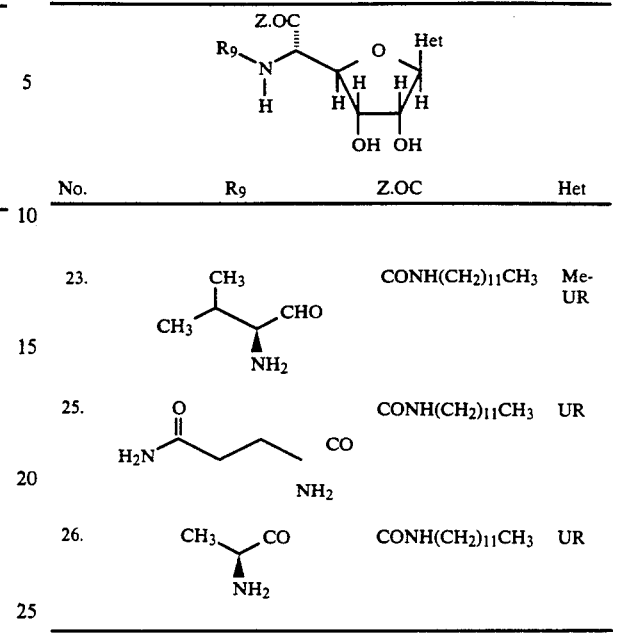

| No. | R9 | Z.OC | Het |
|---|---|---|---|
| 23. | (CH3)2CH-CH(NH2)-CHO | CONH(CH2)11CH3 | Me-UR |
| 25. | H2N-CO-CH2-CH2-CH(NH2)-CO | CONH(CH2)11CH3 | UR |
| 26. | CH3-CH(NH2)-CO | CONH(CH2)11CH3 | UR | or a pharmaceutically acceptable salt of such a compound.

8. A pharmaceutical composition comprising a compound according to claim 1 in combination with a pharmaceutically acceptable carrier material.

9. A method for treating a fungal infection in a mammal which comprises administering to the mammal an anti-fungally effective amount of a compound according to claim 1.

* * * * *